United States Patent [19]

Schaus et al.

[11] Patent Number: 4,471,121

[45] Date of Patent: Sep. 11, 1984

[54] METHOD OF RESOLVING TRANS-D ALPHA-1-N-PROPYL-6-OXODECAHYDROQUINOLINE AND DI-P-TOLUOYLTARTARIC ACID SALTS THEREOF

[75] Inventors: John M. Schaus; Richard N. Booher, both of Indianapolis, Ind.

[73] Assignee: Eli Lilly and Company, Indianapolis, Ind.

[21] Appl. No.: 439,107

[22] Filed: Nov. 3, 1982

[51] Int. Cl.³ .............................................. C07D 471/04
[52] U.S. Cl. .................................. 546/164; 424/258; 546/82

[58] Field of Search ................................. 546/164, 82

[56] References Cited

U.S. PATENT DOCUMENTS 4,198,415 4/1980 Kornfeld et al. ............... 546/165 X
4,230,861 10/1980 Kornfeld et al. ..................... 546/82

Primary Examiner—Richard Raymond
Assistant Examiner—D. B. Springer
Attorney, Agent, or Firm—James L. Rowe; Arthur R. Whale

[57] ABSTRACT

Trans-dl-1-n-propyl-6-oxodecahydroquinoline is resolved via an optically active ditoluoyltartrate salt.

9 Claims, No Drawings

METHOD OF RESOLVING TRANS-D ALPHA-1-N-PROPYL-6-OXODECAHYDROQUINOLINE AND DI-P-TOLUOYLTARTARIC ACID SALTS THEREOF

BACKGROUND OF THE INVENTION

A group of octahydropyrazolo[3,4-g]quinolines are described in Kornfeld and Bach, U.S. Pat. No. 4,198,415, issued Apr. 15, 1980, and in a divisional application thereof, U.S. Pat. No. 4,230,861, issued Oct. 28, 1980. Intermediates or final products of the following structures (Ia and Ib) are disclosed therein.

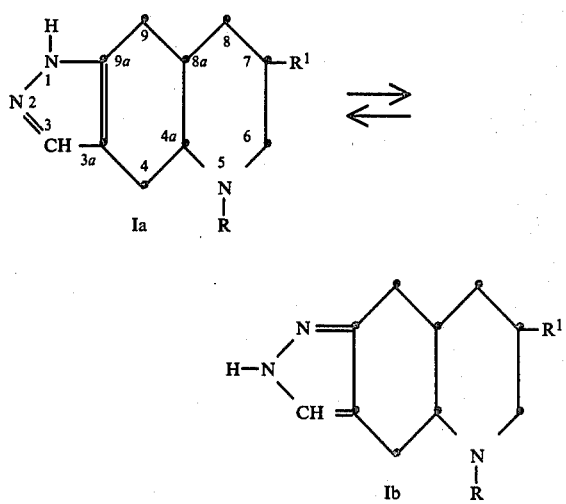

wherein R is H, $C_1$–$C_3$ alkyl, allyl or benzyl, $R^1$ is H or COOZ' and Z' is $C_1$–$C_2$ alkyl or phenyl-substituted $C_1$–$C_2$ alkyl.

The final products disclosed therein are useful as inhibitors of prolactin secretion and in the treatment of Parkinson's syndrome. Of particular interest are compounds wherein $R^1$ is H and R is alkyl, preferably n-propyl.

Compounds according to structures Ia and Ib are disclosed in U.S. Pat. No. 4,198,415 as compound IX in Reaction Scheme I or as compound XV in Reaction Scheme II (where the single tautomer pictured represents both tautomers, as set forth therein). In both reaction schemes, a 6-oxodecahydroquinoline of formula II is converted to the final products Ia and Ib by the following generalized reaction scheme.

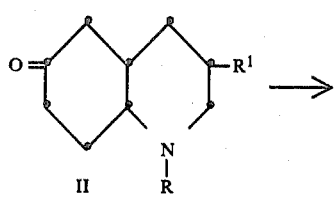

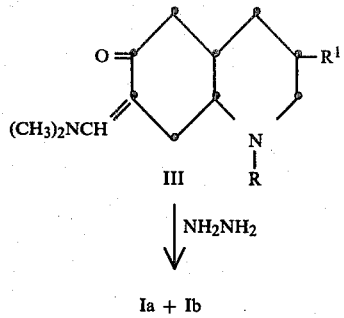

The reagent used to transform the 1-alkyl-6-oxodecahydroquinoline (II) to the intermediate (III) is a dimethylformamide acetal such as dimethyl formamide dimethyl acetal. Structures II and III where R and $R^1$ have their original scope are also claimed in U.S. Pat. No. 4,230,861.

In the copending application of Titus et al., Ser. No. 439,238 filed this even day, a method is disclosed for resolving a tautomeric trans-dl-racemate represented by Ia and Ib where R' is H and R is n-propyl. Also disclosed are the pharmacological properties of one of the isomers, the trans-l or 4aR,8aR isomer, which has substantially all the prolactin inhibiting and anti-Parkinsonism activity of the racemate.

It is an object of this invention to provide an optically active intermediate for use in the preparation of 4aR,-8aR-5n-propyl-4,4a,5,6,7,8,8a,9-octahydro-1H(and 2H)pyrazolo[3,4-g]quinoline.

DESCRIPTION OF THE INVENTION

In fulfillment of the above and other objects, this invention provides a method of resolving trans-dl-1-n-propyl-6-oxodecahydroquinoline represented by the two isomeric structures

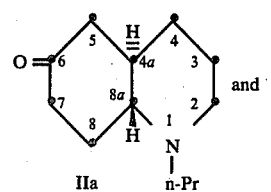

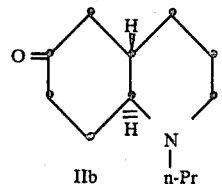

to yield optically pure isomers, each free of the other. This resolution is accomplished using optically active di-p-toluoyltartaric acid as the resolving agent. When (−)-di-p-toluoyltartaric acid is reacted with a solution of the trans racemate, a crystalline salt forms with 4aR,-8aR-1-n-propyl-6-oxodecahydroquinoline. This salt may be separated from the reaction mixture by filtration. The salt of (−)-di-p-toluoyltartaric acid with 4aS,-8aS-1-n-propyl-6-oxodecahydroquinoline (the other enantiomer-IIb) remains in the filtrate. The crystalline salt of the desired enantiomer can be further purified by recrystallization. Optically pure 4aR,8aR-1-n-propyl-6-oxodecahydroquinoline (IIa) is then recovered from the salt by standard procedures. In similar fashion, optically pure 4aS,8aS-1-n-propyl-6-oxo-decahydroquinoline (IIb) can be obtained from racemic trans-dl-1-n-propyl-6-oxodecahydroquinoline by using (+)-di-p-toluoyltartaric acid as the resolving agent.

IIa above is preferably named as 4aR,8aR-1-n-propyl-6-oxodecahydroquinoline but is also correctly named as the trans-l-isomer or the trans-(−) isomer, or as 4aα,8aβ-1-n-propyl-6-oxodecahydroquinoline.

CHOICE OF RESOLVING AGENT

A number of other optically active acids were tried as potential resolving agents. These acids include (+)-tartaric acid, (−)-dibenzoyl tartaric acid, (+)-camphoric acid, (+)-10-camphorsulfonic acid, (−)-mandelic acid, (−)-malic acid, N-acetyl-L-glutamic acid and t-BOC-D-phenyl glycine. These acids either failed to form a crystalline salt with dl-trans-1-propyl-6-oxodecahydroquinoline or, in those cases in which a crystalline salt did form, recrystallization failed to provide an efficient optical purification. Thus, (−)-di-p-toluoyltartaric acid and (+)-di-p-toluoyltartaric acid appear to be unique as readily available, efficient resolving agents for trans-dl-1-n-propyl-6-oxodecahydroquinoline.

CHOICE OF SOLVENT SYSTEMS

Various solvent systems were used in order to determine which gave crystalline salt of high optical purity and yield.

The following table summarizes the solvent systems employed, yield of (−)-di-p-toluoyltartrate salt based on starting trans-dl-ketone, melting point, $[\alpha]_D^{25}$ and $[\alpha]_{365}^{25}$; (both at c=1, MeOH).

TABLE

| Solvent System | Tartrate salt M.P. °C. | No. Recrystallizations | in % yield | $[\alpha]_D^{25}$ | $[\alpha]_{365}^{25}$ |
|---|---|---|---|---|---|
| methylethylketone (MEK) | 146–9 | 0 | 10 | — | — |
| acetonitrile (CH₃CN) | 152–4 | 3 | 20 | −105.39° | −503.39° |
| methylisobutylketone (MIBK) | 156–7 | 3 | 13 | −106.39° | — |
| isopropanol | 151–2 | 3 | | −100.94° | — |
| n-propanol | 155–6 | 2 | 17 | −107.0° | −514.0° |
| MIBK/MeOH | 158–60 | 2 | 26 | −107.8° | −515.6° |
| Ethanol | 158–8 | 2 | 20 | −106.89° | −512.29° |
| CH₃CN/MeOH (10:1) | 157–8 | 1 | 28 | −107.6° | −515.2° |
| methanol | | 0 | 18.7 | −107.49° | |

While all of the solvents listed in the table plus methanol from Example 1 below are operative, we prefer to use the lower straight chain alkanols, methanol, ethanol and n-propanol alone or with methylisobutylketone or acetonitrile. Preferably, a combination of methanol and acetonitrile is used as a solvent for the (−)-di-p-toluoyltartaric acid resolution. Methanol-acetonitrile solvent ratios from 1 to 4 to 1 to 10 have been used although these ratios are not critical as long as a finite percent of methanol is present. In addition, we have found that superior resolution is obtained at salt molarities in the neighborhood of 0.15–0.16 M, although molarities outside of that range are fully operative.

Also part of this invention are the optical isomers 4aR,8aR-1-n-propyl-6-oxodecahydroquinoline (IIa) and 4aS,8aS-1-n-propyl-6-oxodecahydroquinoline (IIb) and acid addition salts thereof.

Such salts include salts derived from inorganic acids such as: hydrochloric acid, nitric acid, phosphoric acid, sulfuric acid, hydrobromic acid, hydriodic acid, phosphorous acid and the like, as well as salts derived from organic acids such as aliphatic mono and dicarboxylic acids, phenyl-substituted alkanoic acids, hydroxy alkanoic and alkandioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate and the like salts.

Preparing the optical isomer of an intermediate, such as 4aR,8aR-1-n-propyl-6-oxodecahydroquinoline, is always advantageous compared with resolving a final product as in Titus et al (loc. cit.) since, in the latter procedure, the inactive isomer, constituting one-half of the starting material, is discarded. It is clearly cheaper to discard starting materials than final products. In addition, the yields for the resolution of 1-n-propyl-6-oxodecahydroquinoline are better than those for the resolution of the pyrazolo[3,4-g]quinoline derived therefrom. In addition, the resolved isomers, both 4aR,8aR and 4aS,8aS-1-n-propyl-6-oxodecahydroquinoline, are potential intermediates for the synthesis of other optically active final products; for example, other heterocyclic rings can be fused to the quinoline ring in addition to the pyrazole system illustrated in the application of Schaus Ser. No. 438,834, filed this even day to yield novel tricyclic systems, thus obviating the necessity of developing resolution methods for each new final product.

The resolution of trans-dl-1-n-propyl-6-oxodecahydroquinoline is illustrated by the following examples.

EXAMPLE 1

Ten g. of (−)-di-p-toluoyltartaric acid were dissolved in 75 ml. of warm methanol. The solution was added to a solution of 5.05 g. of trans-dl-1-n-propyl-6-oxodecahydroquinoline in 15 ml. of methanol. The reaction mixture was brought to a boil and was then allowed to cool to ambient temperature. After remaining at ambient temperature overnight, crystallization was induced by the addition of seed crystals previously obtained. The crystalline tartrate salt was isolated by filtration and the filter cake washed with methanol; yield =2.813 g. (18.7%) of a white crystalline solid comprising the (−)-di-p-toluoyltartrate of 4aR, 8aR-1-n-propyl-6-oxodecahydroquinoline; $[\alpha]_D^{25}$=−107.49° (MeOH, c=1). Recrystallization of the salt from methanol gave 1.943 g. of the optically pure salt, $[\alpha]_D^{25}$=−108.29° (MeOH, c=1). The (−)-di-p-toluoyltartrate salt thus obtained was treated with dilute aqueous sodium hydroxide and the resulting alkaline solution extracted with methylene dichloride. The methylene dichloride extract was dried, concentrated and the solvent removed therefrom in vacuo. The resulting residue was distilled to yield a colorless oil comprising purified 4aR,8aR-1-n-propyl-6-oxodecahydroquinoline; $[\alpha]_D^{25} = -88.51°$ (MeOH, c=1).

Other salts are prepared by dissolving the free base in ether, passing gaseous HCl through the solution or adding an ethereal solution of the acid, and isolating the ether-insoluble salt by filtration. Alternatively, a solution of the free base in a lower alkanol can be mixxed with a solution of the acid in the same solvent, and the soluble salt isolated by evaporation of the solvent.

EXAMPLE 2

Following the procedure of Example 1, 48.8 g. of trans-dl-1-n-propyl-6-oxodecahydroquinoline in 200 ml. of acetonitrile were added to a warm solution of 101 g. of (−)-di-p-toluoyltartaric acid in 1 l. of acetonitrile and 300 ml. of methanol. The mixture was heated to reflux temperature and then allowed to stand at ambient temperature overnight. Seeding produced, as a first crop, 32 g. (22% yield) of 4aR,8aR-1-n-propyl-6-oxodecahydroquinoline (−)-di-p-toluoyltartrate melting at about 158–9° C.; $[\alpha]_D^{25} = -107.5°$. (c=1, MeOH); $[\alpha]_{365}^{25} = -515.5°$. (c=1, MeOH).

The above resolution was also carried out using 41.1 g. of trans-dl-1-n-propyl-6-oxodecahydroquinoline and 80.8 g. of (−)di-p-toluoyltartaric acid monohydrate in 500 ml. of anhydrous methanol. The yield was 34.5 g. (28%); $[\alpha]_D^{25} = -107.3°$; $[\alpha]_{365}^{25} = -512.9°$ (both at c=1, MeOH); optical purity=about 97%

Conversion of the 4aR,8aR-1-n-propyl-6-oxodecahydroquinoline to 4aR,8aR-1-n-propyl-4,4a,5,6,7,8,8a,9- octahydro-1H(and 2H)-pyrazolo [3,4-g]quinoline is conveniently carried out by the method of Schaus, Ser. No. 438,834 filed this even date.

We claim:

1. The process of resolving trans-dl-1-n-proply-6-oxodecahydroquinoline into its component optical isomers which comprises essentially the steps of contacting a solution of the racemate with a solution of an optically active di-p-toluoyltartaric acid, containing at least 0.5 equivalents of the acid, separating the thus-formed salt of the optically active trans-1-n-propyl-6-oxodecahydroquinoline isomer and the optically active di-p-toluoyltartaric acid, treating the thus-formed salt with base and isolating the optically-active trans-1-n-propyl-6-oxodecahydroquinoline isomer therefrom.

2. A process according to claim 1 in which methanol is employed as a solvent.

3. A process according to claim 1 in which the solvent is a methanol/acetonitrile mixture.

4. A process according to claim 1 in which the solvent is a methanol/methylisobutylketone mixture.

5. A process according to claim 3 in which the solvent is a 1 to 4 to 1 to 10 methanol/acetonitrile solvent mixture.

6. A process according to claim 1 in which a salt of 4aR,8aR-1-n-propyl-6-oxodecahydroquinoline is formed with (−)-di-p-toluoyltartaric acid.

7. A process according to claim 1 in which a salt of 4aS,8aS-1-n-propyl-6-oxodecahydroquinoline is formed with (+)-di-p-toluoyltartaric acid.

8. The salt of (−)-di-p-toluoyltartaric acid and 4aR,8aR-1-n-propyl-6-oxadecahydroquinoline.

9. The salt of (+)-di-p-toluoyltartaric acid and 4aS,8aS-1-n-propyl-6-oxodecahydroquinoline.

* * * * *